United States Patent
Merz et al.

(10) Patent No.: US 8,233,957 B2
(45) Date of Patent: Jul. 31, 2012

(54) SENSOR MODULE FOR A CATHETER

(75) Inventors: Matthias Merz, Leuven (BE); Youri Ponomarev, Leuven (BE); Remco Pijnenburg, Hoogeloon (NL)

(73) Assignee: NXP B.V., Eindhoven (NL)

( * ) Notice: Subject to any disclaimer, the term of this patent is extended or adjusted under 35 U.S.C. 154(b) by 375 days.

(21) Appl. No.: 12/523,512

(22) PCT Filed: Jan. 11, 2008

(86) PCT No.: PCT/IB2008/050094
§ 371 (c)(1), (2), (4) Date: Jul. 16, 2009

(87) PCT Pub. No.: WO2008/090485
PCT Pub. Date: Jul. 31, 2008

(65) Prior Publication Data
US 2010/0010327 A1    Jan. 14, 2010

(30) Foreign Application Priority Data
Jan. 25, 2007   (EP) .................................... 07001611

(51) Int. Cl.
*A61B 5/05*   (2006.01)
(52) U.S. Cl. ........ 600/345; 600/547; 600/549; 600/372; 600/509
(58) Field of Classification Search .......... 600/345, 600/549, 547, 509, 372, 302–308, 346–371, 600/481–507, 529–545
See application file for complete search history.

(56) References Cited

U.S. PATENT DOCUMENTS

| | | | |
|---|---|---|---|
| 3,905,889 A * | 9/1975 | Macur et al. ................ 204/414 |
| 5,156,157 A * | 10/1992 | Valenta et al. ............... 600/463 |
| 5,220,920 A * | 6/1993 | Gharib ......................... 600/345 |
| 5,704,353 A | 1/1998 | Kalb et al. |
| 6,176,856 B1 * | 1/2001 | Jandak et al. ................. 606/29 |
| RE38,186 E | 7/2003 | Payne et al. |
| 7,171,252 B1 * | 1/2007 | Scarantino et al. .......... 600/345 |
| 7,393,501 B2 * | 7/2008 | Zumeris et al. ................ 422/20 |
| 2004/0010303 A1 * | 1/2004 | Bolea et al. .................. 607/118 |
| 2004/0193029 A1 * | 9/2004 | Glukhovsky .................. 600/361 |
| 2004/0234954 A1 | 11/2004 | Nusslein et al. |
| 2005/0054905 A1 * | 3/2005 | Corl et al. .................... 600/309 |
| 2005/0256447 A1 | 11/2005 | Richardson et al. |
| 2006/0247692 A1 * | 11/2006 | Yang et al. ...................... 607/9 |
| 2006/0254343 A1 | 11/2006 | Saxena et al. |
| 2007/0191728 A1 * | 8/2007 | Shennib ....................... 600/546 |

FOREIGN PATENT DOCUMENTS
WO   93/06776   4/1993
(Continued)

OTHER PUBLICATIONS

Donlan, Rodney M.; "Biofilms and Device-Associated Infections"; Emerging Infectious Diseases, vol. 7, No. 2; pp. 277-281; 2001.

(Continued)

*Primary Examiner* — Navin Natnithithadha
*Assistant Examiner* — Sunita Reddy

(57) ABSTRACT

A sensor module (130) for a catheter (110), the sensor module (130) comprising a biofilm detection unit (131) adapted for detecting a characteristic of a biofilm (132) and electric circuitry (135, 800) for providing an output signal indicative of a result of the detection.

25 Claims, 3 Drawing Sheets

FOREIGN PATENT DOCUMENTS

| | | |
|---|---|---|
| WO | 93/06776 A | 4/1993 |
| WO | 03/105942 A1 | 12/2003 |
| WO | 2005/113374 A | 12/2005 |
| WO | 2006/000764 A1 | 1/2006 |

OTHER PUBLICATIONS

Maki, D.G., et al; "Engineering Out the Risk of Infection With Urinary Catheters"; Emerging Infectious Diseases, vol. 7, No. 2; 2001.

Crump, J.A., et al; "Intravascular Catheter-Associated Infections"; European Journal of Clinical Microbiology & Infectious Diseases; 19(1), 2000.

Fallis, W.M.; "Monitoring Uniary Bladder Temperature in the Intensive Care Unit: State of the Science"; American Journal of Critical Care II (1); pp. 38-47; 2002.

Ganesh, et al; "Fiber-Optic Sensors for the Estimation of PH Within Natural Biofilms on Metals"; Sensors and Actuators B, Elsevier Sequoia S.A., Lausanne, CH; vol. 123, No. 2; May 6, 2007; pp. 1107-1112; XP022062718; ISSN: 0925-4005.

Nivens, D.E., et al; "Continuous Nondestructive Monitoring of Microbial Biofilsm: A Reviw of Analytical Techniques"; Journal of Industrial Microbiology, Society for Industria Microbiology, vol. 15; Jan. 1, 1995; pp. 263-276; XP001058180; ISSN: 0169-4146.

\* cited by examiner

SENSOR MODULE FOR A CATHETER

FIELD OF THE INVENTION

The invention relates to a sensor module for a catheter.
Moreover, the invention relates to a catheter.
Furthermore, the invention relates to a base station.
Beyond this, the invention relates to a method of operating a sensor module for a catheter.
Furthermore, the invention relates to a program element.
Moreover, the invention relates to a computer-readable medium.

BACKGROUND OF THE INVENTION

In life science, catheters are used which may be configured as a tube that can be inserted into a body cavity duct or vessel. Catheters thereby allow drainage or injection of fluids or access by medical instruments. A catheter may be a thin, flexible tube.

WO 2006/000764 A1 discloses a pH sensor for use in a catheter drainage system. A catheter, drainage bag or connection unit is disclosed comprising such a pH sensor.

WO 2003/105942 A1 discloses an apparatus for controlling the operation of a catheter, the apparatus including an inlet for receiving the output end of a catheter and an outlet for discharging liquid received from the catheter, valve means between the inlet and the outlet for controlling the flow of liquid through the apparatus, sensing means for sensing one or more properties of the liquid in the apparatus, and control means for controlling operation of the valve means in response to a sensed property of the liquid, such as pressure, and/or in response to a predetermined criteria, such as a time interval having elapsed.

U.S. Pat. No. 5,704,353 discloses a system for monitoring the physical and chemical properties of urine in the urinary bladder and functioning of the bladder. For example, the system can include sensors for pressure, temperature, pH, various different chemical constituents of urine, sodium, potassium, glucose, drug markers, drug metabolites, specific gravity, proteins, leukocyte esterase, nitrites, urobilinogen, whole or crenated blood cells, ketones, bilirubin, turbidity or color, the sensors being connected to transmission means for delivering signals representative of the properties detected by the sensors.

However, conventional catheters may cause the risk of CAUTI (catheter-associated urinary tract infection).

OBJECT AND SUMMARY OF THE INVENTION

It is an object of the invention to reduce the risk of catheter-associated infections.

In order to achieve the object defined above, a sensor module for a catheter, a catheter, a base station, a method of operating a sensor module for a catheter, a program element and a computer readable medium according to the independent claims are provided.

According to an exemplary embodiment of the invention, a sensor module for a catheter is provided, the sensor module comprising a biofilm detection unit adapted for detecting a characteristic of a biofilm and comprising electric circuitry for providing an output signal (for instance an electronic, optical or electromagnetic signal) indicative of a result of the detection.

According to another exemplary embodiment of the invention, a catheter is provided comprising a tubular element enclosing a lumen, and a sensor module having the above-mentioned features (functionally) coupled (particularly connected) to the tubular element.

According to still another exemplary embodiment of the invention, a base station is provided comprising a communication unit adapted for communicating with a sensor module having the above mentioned features (particularly adapted for communicating with such a sensor module in accordance with a defined communication protocol which is supported by both the base station and the sensor module and/or in accordance with defined communication addresses of the base station/the sensor module), and an output unit adapted for outputting the result of the detection of the sensor module.

According to still another exemplary embodiment of the invention, a method of operating a sensor module for a catheter is provided, the method comprising detecting a characteristic of a biofilm, and providing an output signal (for instance an electronic, optical or electromagnetic signal) indicative of a result of the detection.

According to still another exemplary embodiment of the invention, a program element (for instance an item of a software library, in source code or in executable code) is provided, which, when being executed by a processor, is adapted to control or carry out a method of operating a sensor module for a catheter having the above mentioned features.

According to yet another exemplary embodiment of the invention, a computer-readable medium (for instance a CD, a DVD, a USB stick, a floppy disk or a harddisk) is provided, in which a computer program is stored which, when being executed by a processor, is adapted to control or carry out a method of operating a sensor module for a catheter having the above mentioned features.

The data processing scheme according to embodiments of the invention can be realized by a computer program, that is by software, or by using one or more special electronic optimization circuits, that is in hardware, or in hybrid form, that is by means of software components and hardware components.

In the context of this application, the term "sensor module" may denote a sensor unit which can be integrated in a tubular catheter or which can be connected between several tubular catheter pieces. Components of the sensor module may be embedded in a catheter wall or may be provided as ring-like components connecting different pieces/segments of the lumen-forming catheter.

The term "biofilm" may particularly denote a structure comprising bacteria and/or microbes which may be embedded in an extracellular polymeric matrix, particularly an extracellular polysaccharide matrix. Such biofilms may be formed when microorganisms attach to living or non-living surfaces, including those of indwelling medical devices (see Rodney M. Donlan, "Biofilms and Device-Associated Infections", Emerging Infectious Diseases, Vol. 7, No. 2, pages 277-281, 2001). More generally, a biofilm may be any layer including biological material, which is indicative of an infection or of a risk of an infection.

The term "electric circuitry" may particularly denote any electronic member, which has the capability of data transport, data supply, data transfer, data conversion or data provision. This may include simple electronic wiring or optoelectronic components such as an optical fiber transporting an optical signal.

The term "processing unit" may particularly denote any (micro-)electronic member which has the capability of data processing and which may generate an electronic signal which represents a presence biofilm characteristic of a sensor module for a catheter. Such a processing unit may be formed using a microprocessor, a CPU (central processing unit), or any other electronic control unit.

The term "output signal" may particularly denote any automatically generated indication of a result of the biofilm detection. Such an output signal may include information for characterizing the biofilm and may form the basis to further process the output signal without the need of an interference of a human user.

According to an exemplary embodiment of the invention, a sensor module for implementation into a tubular catheter wall may be provided which is capable of sensing the presence, absence and/or the extent of a biofilm formed on an interior surface and/or on an exterior surface of the catheter walls, therefore being an indicator for the danger of an infection. In other words, the formation of a biofilm may be considered as a fingerprint of an infection. By automatically (for instance continuously or regularly) monitoring the biofilm characteristics at the surface of the catheter wall, the processing unit may continuously provide electronic signals indicative of the biofilm characteristics for output to a base station. Thus, a patient wearing a catheter even for a long time may always be sure that no infection has occurred unless the sensor module gives notice about the formation of a (sufficiently large) biofilm.

Thus, according to an exemplary embodiment of the invention, an infection monitor for catheters is provided. More particularly, a catheter may be provided having integrated sensor(s)/detector(s) for monitoring sterility such as biofilm formation or microbial growth for early detection of infections.

For this purpose, according to an exemplary embodiment of the invention, a catheter is provided comprising an infection detector for monitoring biofilm formation. The generation of a biofilm may be a reliable indicator for an upcoming infection. According to an exemplary embodiment, the infection detector may be based on a pH-sensitive sensor such as an ISFET (ion sensitive field effect transistor) integrated into a substrate. Additionally or alternatively, the infection detector may be adapted for impedance measurement between a substrate electrode and a reference electrode in a medium, or for impedance measurement using two (or more) substrate-integrated electrodes.

According to an exemplary embodiment of the invention, the infection detector may comprise at least two sensors and a probability analysis unit for generating probability information regarding a detected biofilm formation. The redundant measurement of the biofilm formation may increase reliability, and the provision of a plurality of sensors along an extension of the catheter may allow deriving information regarding a dynamic behaviour of an upcoming infection, such as a growth direction. Thus, the infection detector may allow detecting urinary tract infections at an early stage before it reaches the bladder rather than merely trying to prevent it. Particularly, exemplary embodiments of the invention may be used in the context of urinary catheters or intravascular catheters.

Automatic biofilm detection, for instance by pH and impedance measurements, may allow to detect infections spreading on the inside and/or outside between catheter wall and ureter. This may allow taking into account a spreading of infections along the catheter with measurements at a plurality of positions. Arranging several sensor sides along the catheter allows monitoring spreading of the biofilm and discriminates from common changes caused by different patient's physiology.

An impedance measurement also allows determining a thickness of the biofilm and possible encrustation. Under certain conditions, biofilms may be dangerous only if they are thick enough and detach from the catheter, as a result the catheter may still be used with a thin biofilm for a prolonged time. Therefore, by not only qualitatively but also quantitatively measuring biofilm characteristics, the reliability of the infection warning system may be significantly improved. Exemplary embodiments of the invention may allow for local biofilm detection independent of the pH of the body fluid. This may be advantageous particularly for intravenous catheters: If an infection is only detected if the blood pH changes then it may be too late for the patient.

Exemplary embodiments of the invention allow for one or both of an intraluminal and an extraluminal biofilm detection taking both routes of infection into account.

According to an exemplary embodiment of the invention, an infection monitor for a catheter may be provided for continuously monitoring the sterility of indwelling (urinary) catheters. Integrated pH and/or impedance sensor may allow the detection of potential infections at an early stage such that the catheter can be removed or exchanged just in time to prevent negative effects for the patient.

Additionally or alternatively to the infection detection feature, a catheter integrated body temperature monitor may be provided according to an exemplary embodiment of the invention. Thus, a device for continuously monitoring the body temperature of catheterized patients in intensive care units and nursing homes may be provided. A thermometer and a microprocessor with a memory and an RF unit for data transfer may be integrated into (the tip of) a (urinary) catheter together with an energy source such as a battery. The device continuously measures and records the body temperature (in the human body, for instance in the bladder) and may transfer the data to an external indicator unit at regular intervals.

Next, further exemplary embodiments of the sensor module will be explained. However, these embodiments also apply to the catheter, to the base station, to the method, to the program element and to the computer-readable medium.

The biofilm detection unit may comprise one or more pH sensors, particularly an ion sensitive field effect transistor (ISFET). Using a pH sensor may allow to characterize the formation of a biofilm in a qualitative and/or quantitative manner with high accuracy. This may allow detecting infections at an early stage.

Additionally or alternatively, the biofilm detection unit may comprise one or more impedance sensors. Such an impedance sensor may be adapted for a measurement of the impedance (including an ohmic resistance or a capacitive impedance or an inductive impedance) between two electrodes, for instance by a first electrode integrated in a substrate on the one hand and a second electrode integrated in the substrate or located in a medium surrounding the sensor module on the other hand.

The impedance sensor may be adapted for an impedance measurement involving more than two electrodes, for instance implementing four electrodes arranged in a (for instance linearly aligned) configuration with two outer electrodes and two inner electrodes arranged between the two outer electrodes, wherein the electrodes may be integrated in or attached to a substrate of the sensor module. The impedance sensor may then be adapted for applying an exciting signal such as an alternating electric signal between the outer electrodes and for measuring an electric response signal between the two inner electrodes, the electric response signal being indicative of the impedance value. Thus, impedance measurements may be done with a 4-electrode configuration further reducing/eliminating electrode polarization effects or change in electrode properties. In such a configuration, 4 electrodes may be arranged (in a row) on the substrate. AC current may be applied between the outer electrodes and voltage may be measured between the two inner electrodes. Thus, a reliable and early detection of anomalies resulting from an upcoming infection in an environment of the catheter may be ensured.

The processing unit may be adapted for generating probability information regarding a reliability of the detected characteristic of a biofilm. Under undesired circumstances, the mere formation of a change of the impedance and/or of the pH level of a single sensor may have origins, which differ from a biofilm formation. However, by combining different measurements of different measurement methods (impedance and/or pH) and of sensors located at different positions along the catheter, a redundant and complementary information may be obtained which allows to eliminate artifacts and to formulate qualitative and/or quantitative statements regarding the static and/or dynamic behavior of the biofilm.

The processing unit may be adapted for generating the electronic output signal at regular time intervals, or (quasi-) continuously. Particularly, the processing unit may work autonomously without the necessity of a human being to contribute to the measurement. Particularly, it may be dispensable according to exemplary embodiments of the invention that a human user evaluates a surface of the sensor module, for instance by perceiving a colour change or the like. In contrast to this, the processing unit may electronically determine the biofilm characteristics from time to time (for instance every 5 minutes or once an hour or once a day) and may monitor the actual biofilm characteristic.

The processing unit may be adapted for generating the electronic output signal comprising a unique identifier. Such a unique identifier identifying a sensor module may be attached to the measurement data and may allow a plurality of sensor modules to be used with a single base station being communicatively coupled with the individual sensor modules. The unique identifier (for instance of an RFID tag) may directly assign the measurement to a specific position or detector of a complex sensor system.

The sensor module may comprise a communication unit adapted for transmitting the electronic output signal to a base station. Such a base station may be provided externally of a human body, i.e. apart from the catheter. The base station may have a display unit and an input element such as control buttons, which may allow a human to be informed about the present biofilm formation characteristic.

The communication between the sensor module and such a base station may be performed in a wired manner, for instance using a cable or an optical fiber aligned along a lumen of the catheter or embedded within catheter walls. Alternatively, a wireless communication may be performed using optical signal transmission, infrared signal transmission, UV signal transmission, or high-frequency (RF) detection techniques. For example, an RFID communication or a Bluetooth communication may be made possible between the sensor module and the base station.

At least a part of the sensor module may be monolithically integrated in semiconductor technology. Therefore, a part of the sensor module or the entire sensor module may be provided as an integrated circuit (IC). Such an integrated circuit may be formed in silicon technology or using any other group IV semiconductor technology such as germanium technology. Alternatively, the integrated circuit may be manufactured in group III-group V semiconductor technologies such as gallium arsenide technology.

The sensor module may comprise a temperature detection unit adapted for detecting a temperature signal, wherein either the processing unit evaluating also the biofilm formation or a separate processing unit may be adapted for processing the temperature signal for generating an (electronic) output signal indicative of the temperature. Thus, systems according to an exemplary embodiment of the invention may also allow to continuously monitor the temperature development at a position of the sensor module, for instance within a human body into which a catheter has been inserted. Particularly, a device according to an exemplary embodiment of the invention may contain only a temperature sensor, but no biofilm detector. Such a device might be interesting for short-term catheterization, for example of intensive care patients.

The sensor module may comprise a memory adapted for storing data. Thus, the sensor module may also have an integrated memory for storing data. Data may be sent to the base station at regular or irregular intervals upon request from the base station, for instance when a doctor/nurse comes for a visit with the base station to a patient carrying a sensor module in a catheter.

The sensor module may comprise a power supply unit adapted for supplying at least a part of the components of the sensor module with electric energy, particularly realized as at least one of the group consisting of a disposable/substitutable battery, and a rechargeable battery rechargeable in a wireless (for instance inductive or capacitive) manner or in a wired manner. Examples of an appropriate power supply are a primary battery or a rechargeable battery recharged by energy transfer via an RF/inductive link.

Next, further exemplary embodiments of the catheter will be explained. However, these embodiments also apply to the sensor module, to the base station, to the method, to the program element and to the computer-readable medium.

The sensor module may be integrated between individual components or segments of the tubular element. For example, different tube segments may sandwich a sensor module which may have a ring-like shape and which may form, together with hollow cylindrical tubular elements, a common sealed lumen.

The catheter may further comprise a collection bag being in fluid communication with the lumen of the tubular element. In such a collection bag, body fluid or any other fluid may be collected.

Particularly, the catheter may be adapted as a urinary catheter. However, alternative applications are possible such as the insertion of the catheter into a blood vessel.

Providing a plurality of sensor modules of the above-described type and locating them along the tubular element of the catheter may allow to derive a spatially dependent biofilm formation information.

The sensor module may be adapted for detecting a characteristic of a biofilm formed in an intraluminal surface and/or in an extraluminal surface of the tubular element. Therefore, both surface portions of the tubular element may be monitored using catheter according to an exemplary embodiment of the invention. This may allow to locate position and origin of the infection.

At least a part of a surface of the catheter may comprise an infection-inhibiting functionalization. Such an infection-inhibiting functionalization of a surface of the catheter may include covering the surface with antimicrobial substances such as silver particles or an appropriate medication. Therefore, an upcoming infection may not only be detected in an early stage but also may be prevented or inhibited.

Next, a further exemplary embodiment of the base station will be explained. However, this embodiment also applies to the sensor module, to the catheter, to the method, to the program element and to the computer-readable medium.

The base station may comprise a programming unit adapted for programming the sensor module, particularly adapted for involving bidirectional communication between the sensor module and the base station. This may allow for programming the sensor module by an external device (involving two way communication from module to base station for data transfer, and from programmer unit, for instance base station, to the module for programming, for instance to set the intervals between measurements). Moreover, the module can send data on its status, for instance battery level, to the base unit, or vice versa.

The aspects defined above and further aspects of the invention are apparent from the examples of embodiment to be described hereinafter and are explained with reference to these examples of embodiment.

BRIEF DESCRIPTION OF THE DRAWINGS

The invention will be described in more detail hereinafter with reference to examples of embodiment but to which the invention is not limited.

DESCRIPTION OF EMBODIMENTS

Figure 1:
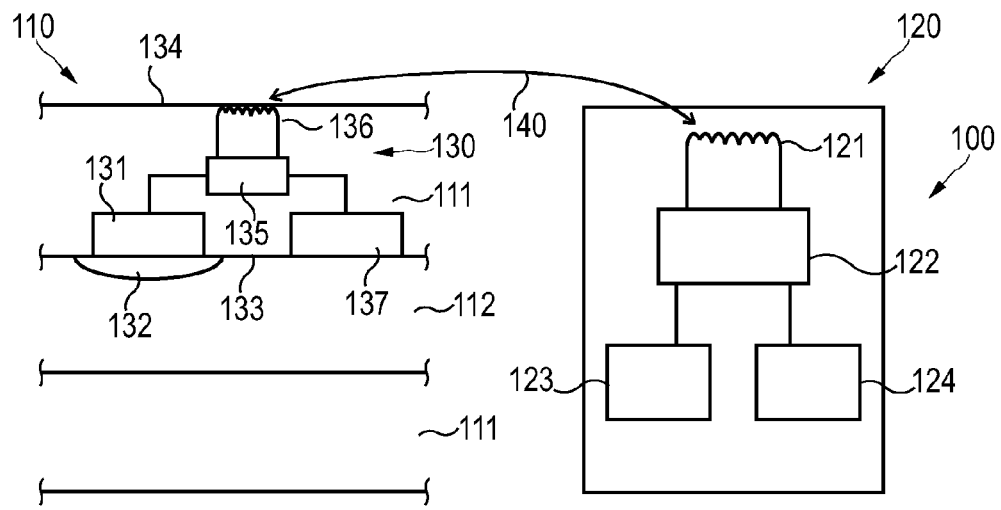
FIG. 1 illustrates a catheter system according to an exemplary embodiment of the invention.

The illustration in the drawing is schematical. In different drawings, similar or identical elements are provided with the same reference signs.

In the following, referring to FIG. 1, a catheter system 100 according to an exemplary embodiment of the invention will be explained.

The catheter system 100 comprises a catheter 110 (only a part thereof is shown in FIG. 1) and a base station 120 which are coupled for wireless communication 140.

The catheter 110 (FIG. 1 shows a cross section thereof) comprises a tubular wall 111 defining a lumen 112. In one wall of the tubular element 111, a sensor module 130 is embedded.

The sensor module 130 comprises a biofilm detection unit 131 adapted for detecting a characteristic of a growing biofilm 132, which is formed according to FIG. 1 at an intraluminal surface 133 of the tubular element 111. Also an extraluminal surface 134 can be a surface on which a biofilm 132 may be formed and detected (not shown in FIG. 1).

The biofilm detection unit 131 is adapted for detecting a characteristic (such as a thickness, a chemical property, a length, a grow speed) of the biofilm 132. The biofilm detection unit 131 is coupled to a processing unit 135, such as a microprocessor, which may perform signal processing of the characteristic detected by the biofilm detection unit 131 for generating an electronic output signal indicative of the result of the detection. The biofilm detection unit 131 may be a pH sensor or an impedance sensor.

The processing unit 135 may evaluate the detection signals of the biofilm detection unit 131 qualitatively and quantitatively and may generate an electronic output signal at regular time intervals, for instance every 5 minutes.

Since the base station 120 may communicate with a plurality of sensor modules 130 (only one is shown in FIG. 1), a unique identifier unambiguously identifying the sensor module 130 may be attached to the electronic output signal by the processing unit 135.

An inductive communication unit 136 (transmitter/receiver), in the present embodiment a transmission coil 136, is connected to the processing unit 135 and allows for a wireless transmission of the generated output signal together with the unique identifier via a schematically illustrated wireless communication path 140 to a corresponding coil 121 of the base station 120.

Furthermore, the sensor module 130 comprises a temperature detection unit 137 for locally detecting a temperature signal at the interior wall surface 133 of the tubular wall element 111. The temperature detection unit 137 also supplies the detected temperature signal to the processing unit 135 for processing the temperature signal for generating an electronic output signal indicative of the actual temperature. Also this temperature signal may be transmitted via the coils 136, 121 from the sensor module 130 to the base station 120.

The base station 120 furthermore comprises a processing unit 122 such as a CPU (central processing unit) for further processing the electronic output signals provided via the communication path 140. Corresponding detection results may be output, visible or audible for a human user, using an output unit 123 such as a display like an LCD. Alternatively, an acoustic output is possible.

Beyond this, an input unit 124 is provided which allows a user to communicate with a base station 120, for instance to input control commands. The input unit 124 may include input elements such as one or more buttons, a keypad, a joystick, or may even be a microphone of a voice recognition system.

Before further exemplary embodiments of the invention will be discussed, some recognition of the inventors will be explained based on which embodiments of the invention have been developed.

Indwelling urinary catheters have become one of the most commonly used medical devices in hospitals, long-term care facilities, and the home. Alone in the US, urinary catheters are inserted into more than 5 million patients in acute care hospitals and extended care facilities every year (about 20 to 25 millions are sold in the USA every year). Despite this widespread use, the devices are not free of risk. More than one million patients in the United States acquire a catheter associated urinary tract infection (CAUTI) every year. This is 20% of all patients that receive such a catheter. CAUTI is the most common nosocomial infection (that is to say infection which results from treatment in a hospital or hospital-like setting) and the second most common source of nosocomial blood stream infections.

Studies suggest that patients with CAUTI have an increased death rate, unrelated to the development of urosepsis. Although most CAUTIs are asymptomatic, creating little additional discomfort, its treatment (usually with antibiotics) may impose an extra burden to the patient's body. Moreover, detected cases of CAUTI cause an extra to the direct cost of accurate care hospitalization and may involve unnecessary microbial drug therapy. CAUTIs comprise perhaps the largest institutional reservoir of nosocomial antibiotic resistant pathogens, which is a severe issue in modern acute and extended care facilities (see D. G. Maki, P. A. Tambyah, "Engineering out the risk of infection with urinary catheters", Emerging Infectious Diseases, Vol. 7, No. 2, 2001).

Furthermore, many patients using catheters are also in need of (constant or regular) monitoring of their body temperature.

Figure 2:
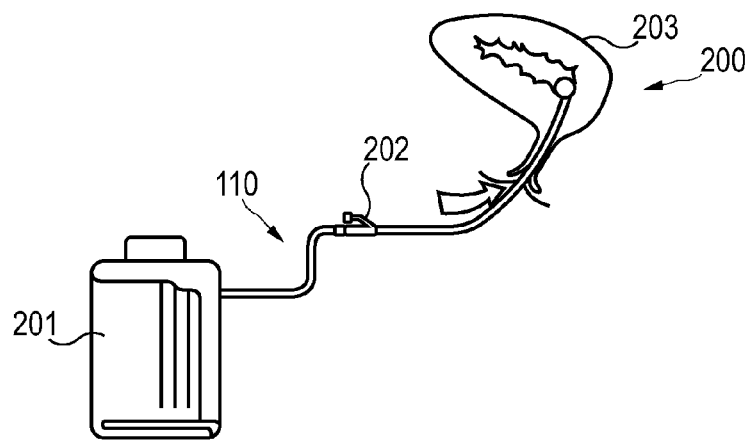
FIG. 2 illustrates a catheter system as well as routes of entry of uropathogens to a catheterized urinary tract.

FIG. 2 shows a catheter system 200 illustrating a collection bag 201 for collecting urine, a catheter 110 having a valve 202 and being inserted into a bladder 203 of a human patient.

As shown in FIG. 2, organisms may gain access to the urinary tract in two ways, extraluminal or intraluminal. Extraluminal contamination may occur early, by direct inoculation when the catheter is inserted, or later, by organisms ascending from the perineum by capillary action. Intraluminal contamination occurs by reflux of microorganisms gaining access to the catheter lumen from failure of closed drainage or contamination of urine in the collection bag 201.

In order to reduce or eliminate CAUTI, urinal catheters have been developed which are impregnated with antiseptic solutions and antimicrobial drugs or coated with a silver alloy hydrogel. These coatings significantly reduce the risk of CAUTI for short-term catheterizations not exceeding 2 to 3 weeks, for example silver hydrogel catheters reduce the incidents of CAUTI by 40% (25.7 versus 15.4 per 100 catheters, see the above cited Maki et al. 2001). Despite this success, the number of CAUTI still remains unacceptably large (at a 40% reduction, still 12% of all catheterized patients will acquire an infection).

Unlike conventional approaches, exemplary embodiments of the invention aim at detecting urinary tract infection at an early stage before it reaches the bladder, rather than trying to prevent it. In this way, the catheter can be removed just in time to prevent further spreading and the infection can be stopped with little effort, for example by applying antimicrobial ointment to the urethra or rinsing with antimicrobial solution.

Urine cultures obtained from the drainage bags may be used for monitoring the development of an infection. This technique is expensive and time-consuming since it takes several hours to days until a result is obtained. During that time, the infection can further spread out. Even more important is that the infection might only be detected if it has already reached the bladder because only then enough bacteria may be present in the collected urine for conventional detection.

According to an exemplary embodiment of the invention, one or more infection detectors 131 may be integrated into or between catheter walls 111. Since catheter infections are always associated with the presence of biofilms 132 on the surface 133, these biofilms 132 may be taken as reliable indicators for infections. Biofilm may comprise bacteria and microbes embedded in an extracellular polysaccharide matrix. This matrix may transport nutrients and metabolites and may protect the bacteria from external influences. In other words, bacteria encased in a biofilm 132 can withstand far higher antibiotic concentrations (for instance up to 10 to 100 times higher) then freely moving bacteria.

Due to the encapsulation, the local environment in the biofilm 132 may be different from that in the surrounding medium. For example, metabolites may change the local pH value at the interface of the biofilm 132/substrate 111 (catheter wall) as compared to the medium/substrate 111 interface. These changes can be recorded with a pH sensitive sensor 131 such as an ISFET (ion sensitive field effect transistor) integrated into the substrate 111.

Figure 3:
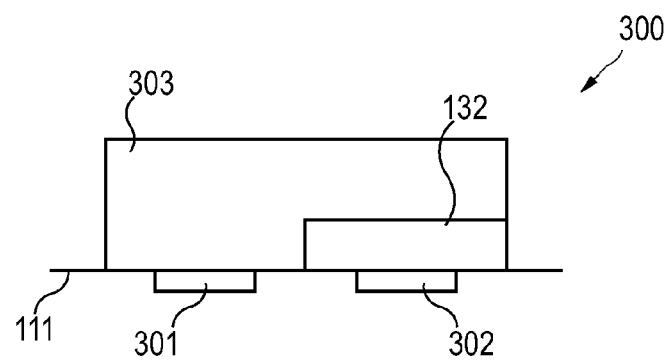
FIG. 3 and FIG. 4 schematically illustrate biofilm detection arrangements according to exemplary embodiments of the invention.

FIG. 3 shows a scheme 300 illustrating detection of biofilm 132 by pH measurements performed by a first pH sensor 301 and a second pH sensor 302.

In a medium 303 surrounding a catheter wall 111, a first pH value may be present, which may be detected by the first pH sensor 301. The formation of the biofilm 132 on a surface of the second sensor 302 allows the second sensor 302 to detect a second pH value of the biofilm 132, which differs significantly from that of the medium 303.

As shown in FIG. 3, the first sensor 301 measures the pH value of the medium 303, whereas the second sensor 302 measures the pH at the interface to the biofilm 132.

Further, biofilms 132 generally have different electrical properties than the medium 303 they are surrounded with.

Figure 4:
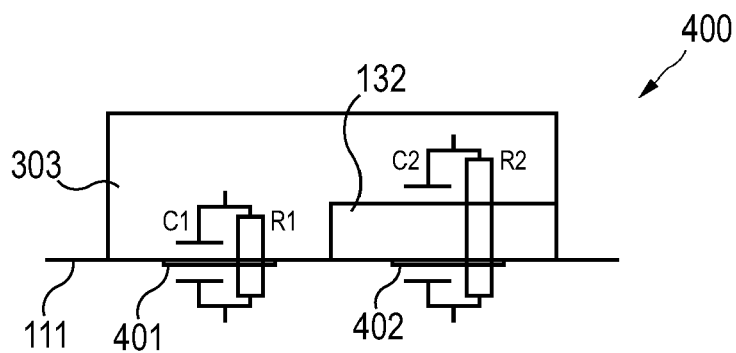

FIG. 4 illustrates a scheme 400 of detection of biofilm 132 by impedance measurements.

A first electrode 401 is in direct contact with the medium 303, whereas a second electrode 402 is in contact with and is covered by the biofilm 132. As schematically indicated in FIG. 4, the biofilm-coated electrode 402 has another impedance (parallel circuit of a resistor R2 and a capacitor C2) than the blank electrode 401 (parallel circuit of R1, C1).

In other words, the electrode 402 covered by the biofilm 132 has another electrical impedance than the clear electrode 401, this is indicated by the different R and C values in the equivalent circuit shown in FIG. 4. Electrode 401 is in direct contact with the medium 303, electrode 402 is covered by the biofilm 132.

This shows that impedance measurements are a proper technique for monitoring biofilm formation (impedance based biofilm/bacteria detectors are commercially available). The impedance may be measured between the substrate electrode and a reference electrode in the medium or using two (or more) substrate-integrated electrodes.

In order to improve the accuracy and reliability of the detection system, both sensor types (pH sensors and impedance sensors) can be integrated simultaneously. Errors, for instance when a change in urine pH is misleadingly interpreted as biofilm formation, can be reduced or minimized by taking the spreading direction of the infection into account. Except for infections caused by an unsterile catheter insertion procedure, all infections (extra- and intraluminal) progress from the outside of the patient's body through the ureter towards the bladder. This means that sensors located more towards the body exterior may detect the biofilm earlier than sensors close to the bladder (further up to the catheter). With this approach, infections can be discriminated from general changes of the patients physiologically, for instance all sensors along the catheter may detect urine pH change simultaneously.

FIG. 5 to FIG. 8 show an autonomous sensor module 500 integrated in a catheter 600 as well as an indicator unit or base station 700.

Figure 5:
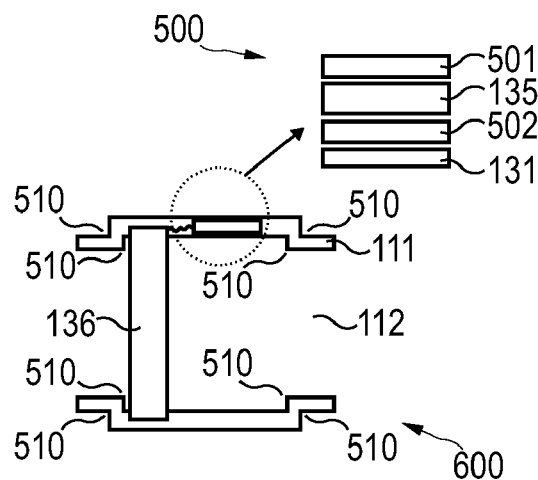
FIG. 5 to FIG. 8 illustrate components of a catheter system according to an exemplary embodiment of the invention.

FIG. 5 shows the autonomous sensor module 500 with a first sensor 131 provided at an inner surface of the tubular wall 111 of the catheter 600 further comprising a processor 135 as well as an RF link and power supply unit 502. A second sensor 501 is provided at an outer surface of the tubular wall 111 of the catheter 600.

Figure 6:
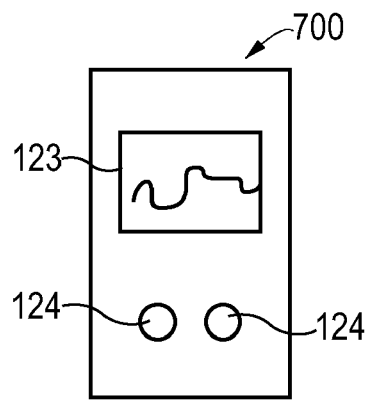

FIG. 6 shows the external indicator unit 700.

Figure 7:
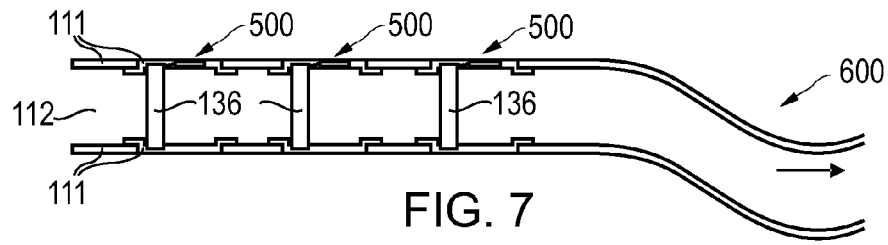

FIG. 7 shows an integration of three sensor modules 500 into a catheter 600.

Figure 8:
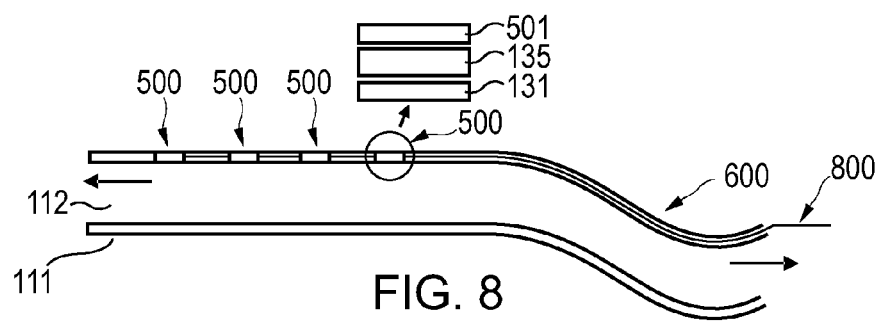

FIG. 8 shows a very simple embodiment having a wire connection 800 for transporting signals detected by the sensors 131, 501 of the sensor modules 500.

According to the embodiments of FIG. 5 to FIG. 8, the sensor data is recorded at regular intervals, buffered in a local memory of the processor 135 and sent to the external indicator unit 700 (for instance when a care person makes a visit). The external indicator unit 700 stores the data and indicates the onset of an infection. Every sensor module 500 has a unique code such that it can be assigned to a single patient. Then, the indicator unit 700 can be used for many patients, for instance only one indicator unit 700 is sufficient for an entire ward.

If several detectors 500 are integrated in a catheter 600 to reduce or minimize false alarms, the necessary data processing may be performed partially or completely in the indicator unit 700. The processor capability can also be integrated partially or completely in the catheter 600 (that is to say in the processing unit 135). The coding of every module 500 again allows the assignment of a specific position in the catheter 600.

The modules 500 may be made by sealing the sensor elements 131, 501 (for instance pH and impedance sensors) into a small cylinder (which may be made of PVC, PE, Latex, silicone, etc.) together with the processor 135, the power and RF unit 502 and antenna or coil 136. The processor 135 may perform A/D conversion, memory functions, etc.

Power may be provided by a primary battery (which may be preferred since catheters may be single use devices usually not used longer than 30 days), a rechargeable battery or by inductive energy transfer (can also be used to recharge an accumulator). In the latter case, recharging may be done within an external power transfer unit that can be integrated in the indicator unit 700. Depending on the configuration of the RF antenna or coil 136 for data transmission, it may also be used for power transfer. Alternatively, a separate antenna/coil may be used for power transfer, and a separate antenna/coil may be used for data transmission.

The sensor(s) 131, 501, processor 135, memory and RF unit may be produced by a semiconductor/CMOS technology. They can be integrated into a single die, or processed separately and then stacked (die bonding) or connected by wires and sealed into a polymer matrix to stabilize and protect the components. Wires may connect a separate battery. Alternatively a die-integrated solid-state (rechargeable) battery can be used. RF communication may be performed via a coil or antenna 136. It can be separated as shown in FIG. 5 or integrated into the dies. Sensors 131, 501 may be present at the inner and/or outer walls of the catheter 600 since infections may progress via both channels intraluminal and extraluminal. Except for the sensor area itself, which may have direct contact with the same environments than the catheter walls (ureter, urine), all other components may be hermetically sealed within the cylinder.

The complete sensor module 500 may be connected or glued to the catheter tube 111 (indicated by small noses 510 in FIG. 5) at a location that lies in the ureter after insertion of catheter 600 into a human body.

FIG. 7 depicts a catheter 600 with three integrated autonomous sensor modules 500 allowing monitoring the spreading of infections into the bladder and eliminating detection errors.

Similarly, several sensor sides can be integrated into a single yet maybe larger/longer module. In that way, infection spreading can still be monitored but at even lower cost. However, if the element gets too long it may create discomfort for the patients since it may be stiffer compared to the catheter tube 111 (as a solution, it is possible to realize all components with thin, flexible silicon and encapsulated in a flexible matrix).

In the very simple embodiment shown in FIG. 8, merely the sensors 500 (optional also local processors 135) may be integrated into the catheter 600. Wires 800 (running in the catheter walls 111, or intraluminal) connect them in a wired manner to the indicator unit 700 (with power supply and memory) that can be part of the collection bag or can be connected to the catheter with a special plug.

The catheter 600 can further be impregnated with antimicrobial drugs or coated with silver alloy hydrogels to reduce the risk of infection.

Although most data and examples provided so far relate to urinary catheters, systems according to exemplary embodiments of the invention are not restricted to this application. Serious infections may also occur with intravascular catheters. Available data suggest there are likely to be more than 500,000 cases of catheter-associated blood stream infections occurring annually in Western Europe and the United States. These may be associated with as many as 100,000 deaths (see J. A. Crump, P. J. Collignon, "Intravascular catheter-associated infections", European Journal of Clinical Microbiology & Infectious Diseases, 19(1), 2000). Detection of these infections may be very difficult especially if the biofilm adheres to the intraluminal side of the catheter. Issues and challenges for intravascular catheters are basically the same as for the urinary catheters. However, the intravascular catheters may have a smaller diameter, so the sensor module may need further miniaturization. Also the regulatory requirements may be higher since these catheters may be in direct contact with blood.

So far, primarily biofilm detection has been explained. However, temperature measurement integrated in the catheter may be provided as well by exemplary embodiments of the invention.

Body temperature measurement is possible with various thermometer configurations and types (mercury, digital, infrared, etc.) as well as different points and orifices where a human body temperature is measured (mouth, rectum, axilla, etc.). Despite its simplicity, body temperature measurement may take some time and may create discomfort for the patient (the wide spread infrared thermometers may be quick with a measurement yet they are often not accurate enough). These issues may become particularly relevant if patients need constant temperature monitoring involving frequent measurements, for instance in an intensive care unit.

Essentially no additional discomfort is created with an integrated temperature measurement according to exemplary embodiments of the invention, since an already existing access to the human body, namely a (urinary) catheter, may be used. Moreover, the constant and automatic monitoring does not require extra attention saving time for the care person and money for the hospitals.

Body temperature measurement with urinary and other catheters has been thoroughly investigated by extensive research studies and is already used in many hospitals (see W. M. Phallis, "Monitoring urinary bladder temperature in the intensive care unit: state of the science", American Journal of Critical Care 11(1):38-47, 2002). Presumably, these catheter-integrated temperature sensors may be connected to an external electronic unit by an ordinary wire connection. Thus, the application involves extra effort for connecting and handling the wires, which may also cause additional risk of infection (CAUTI).

According to an exemplary embodiment of the invention, an autonomous temperature monitor module may be integrated in a catheter, particularly near the tip of a (urinary) catheter. Since the module is fully autonomous, no wires are needed, and the recorded temperature values may be sent to an indicator unit via an RF link.

Figure 9:
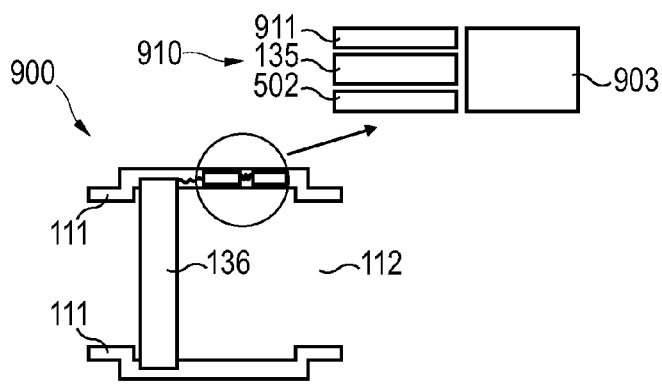
FIG. 9 to FIG. 11 illustrate components of a catheter system according to an exemplary embodiment of the invention.

FIG. 9 shows an autonomous temperature sensor module 910 integrated in a catheter 900.

Figure 10:
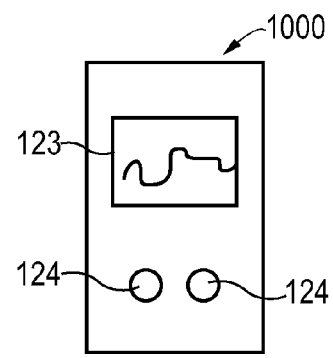

FIG. 10 shows an external indicator unit 1000, which is very similar to the indicator unit 700 shown in FIG. 6.

Figure 11:
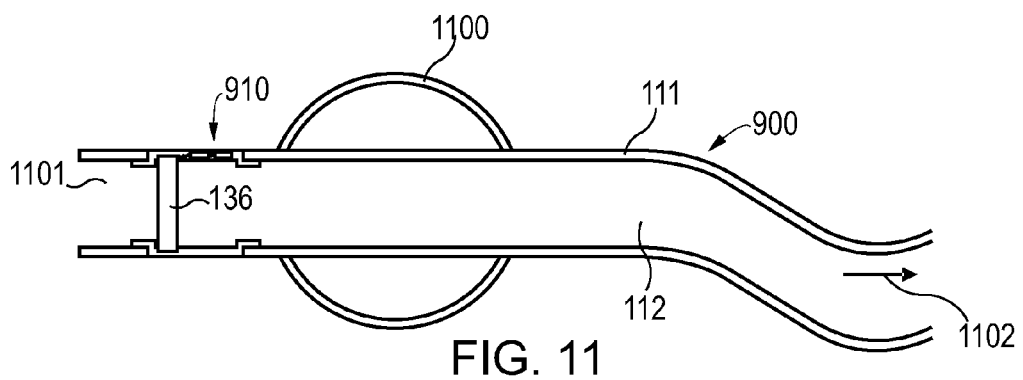

FIG. 11 shows the entire catheter 900 having a balloon 1100. A tip is indicated with reference numeral 1101, and an arrow 1102 indicates a direction towards a collection bag.

Referring to FIG. 9, an autonomous sensor module 910 is shown incorporating a thermometer 911, a processor 135, a memory and RF unit 502 with a transmission coil or antenna 136 as well as a battery 903 for power supply.

Body temperature may be measured at regular intervals, buffered in the local memory and sent to the external indicator unit 1000 (for instance when the care person makes a visit) which may store the data, display the temperature chart at the display 123 and may give a warning signal (optical and/or acoustic) if temperature limits are exceeded (sensor module 910 may also be connected to other intensive care instruments).

Every sensor module 910 may have a unique code such that it can be assigned to a single patient, and the indicator unit 1000 can be used for many patients, for instance only one indicator unit may be needed for an entire ward.

The above described embodiments regarding integration of the biofilm formation sensor 131 into the catheter 600 correspondingly apply to the integration of the temperature sensor 911 into the catheter 900.

The temperature sensor 911 may be produced in semiconductor/CMOS technology. Temperature measurement may be integrated in an electronic chip or may be provided as a discrete sensor element (for instance a Pt100 sensor). Therefore, body temperature monitoring of catheterized patients may be made possible. Instead of urinary catheters, the autonomous temperature sensor module 910 can also be integrated into other temporarily indwelling medical devices such as pulmonary catheters.

Finally, it should be noted that the above-mentioned embodiments illustrate rather than limit the invention, and that those skilled in the art will be capable of designing many alternative embodiments without departing from the scope of the invention as defined by the appended claims. In the claims, any reference signs placed in parentheses shall not be construed as limiting the claims. The word "comprising" and "comprises", and the like, does not exclude the presence of elements or steps other than those listed in any claim or the specification as a whole. The singular reference of an element does not exclude the plural reference of such elements and vice-versa. In a device claim enumerating several means, several of these means may be embodied by one and the same item of software or hardware. The mere fact that certain measures are recited in mutually different dependent claims does not indicate that a combination of these measures cannot be used to advantage.

The invention claimed is:

1. A catheter, the catheter comprising:
a tubular element enclosing a lumen;
a plurality of sensor modules spread out spatially along the length of the tubular element, wherein each of the sensor modules comprises:
a biofilm detection unit configured to detect a characteristic of a biofilm, wherein the biofilm detection unit includes a first sensor located at an inner surface of a tubular wall of the catheter and a second sensor located at an outer surface of the tubular wall of the catheter;
electric circuitry configured to provide an output signal indicative of a result of the detection,
wherein one of the sensor modules comprises a processing unit integrated in a tubular wall of the tubular element sandwiched between the first sensor and the second sensor, and wherein the plurality of sensor modules enable determination of a spatial dependence in the formation of the biofilm.

2. The catheter of claim 1,
wherein the processing unit is configured to process the characteristic for generating the output signal.

3. The catheter of claim 2,
wherein the processing unit is configured to generate a probability information regarding a reliability of the detected characteristic of the biofilm.

4. The catheter of claim 2,
wherein the processing unit is configured to generate the output signal continuously or at regular time intervals.

5. The catheter of claim 2,
wherein the processing unit is configured to generate the output signal comprising a unique identifier.

6. The catheter of claim 1,
wherein at least one biofilm detection unit comprises an ion sensitive field effect transistor.

7. The catheter of claim 1,
wherein at least one biofilm detection unit comprises an impedance sensor.

8. The catheter of claim 7,
wherein the impedance sensor is configured to perform a measurement between at least one first electrode integrated in a substrate and at least one second electrode integrated in the substrate or located in a medium surrounding the sensor module.

9. The catheter of claim 7,
wherein the impedance sensor is configured to perform a measurement between four electrodes arranged in a configuration with two outer electrodes and two inner electrodes arranged between the two outer electrodes;
wherein the impedance sensor is configured to apply an alternating electric signal between the outer electrodes and is configured to measure an electric response signal between the two inner electrodes indicative of the impedance value.

10. The catheter of claim 1,
comprising a communication unit configured to transmit, in a wired or wireless manner, the output signal to a base station.

11. The catheter of claim 1,
wherein at least a part of each sensor module is monolithically integrated in semiconductor technology.

12. The catheter of claim 1, wherein each of the sensor modules comprises a temperature detection unit configured to detect a temperature signal;
wherein the electric circuitry of the sensor module is configured to provide an output signal indicative of a result of the temperature detection.

13. The catheter of claim 1, wherein each sensor module comprises a memory configured to store data.

14. The catheter of claim 1,
further comprising a power supply unit configured to supply at least a part of the components of the plurality of sensor modules with electric energy, wherein the power supply unit comprises a rechargeable battery rechargeable in a wireless manner.

15. The catheter of claim 1, wherein each sensor module is configured to perform a bidirectional communication with an external programming unit for programming the sensor module.

16. The catheter of claim 1,
comprising a collection bag in fluid communication with the lumen of the tubular element.

17. The catheter of claim 1, wherein at least one biofilm detection unit is located at an outer surface of a tubular wall of the tubular element.

18. The catheter of claim 1,
wherein one of the sensor modules is configured to detect a characteristic of a biofilm formed in at least one of the group consisting of an intraluminal surface and an extraluminal surface of the tubular element.

19. The catheter of claim 1,
wherein at least a part of a surface of the catheter comprises an infection-inhibiting functionalization.

20. A base station, the base station comprising
a communication unit configured to communicate with a sensor module of claim 1;
an output unit configured to output the result of the detection of the sensor module.

21. The base station of claim 20,
comprising a programming unit configured to program the sensor module for bidirectional communication between the sensor module and the base station.

22. A method of operating a catheter, the method comprising:
detecting a characteristic of a biofilm using a plurality of sensor modules spread out spatially along the length of a tubular element of the catheter, wherein each of the sensor modules includes a first sensor located at an inner surface of a tubular wall of the catheter and a second sensor located at an outer surface of the tubular wall of the catheter, wherein one of the sensor modules comprises a processing unit integrated in a tubular wall of the tubular element sandwiched between the first sensor and the second sensor;
providing output signals indicative of a result of the detection; and
deriving spatially dependent biofilm formation information from the output signals using a processor.

23. A program element embodied in a non-transitory computer-readable medium, which, when being executed by a processor, is configured to control or carry out a method of claim 22 of operating a sensor module for a catheter.

24. A non-transitory computer-readable medium, in which a computer program is stored which, when being executed by a processor, is configured to control or carry out a method of claim 22 of operating a sensor module for a catheter.

25. A catheter, the catheter comprising
a tubular element enclosing a lumen;
a sensor module coupled to the tubular element, the sensor module comprising
a biofilm detection unit configured to detect a characteristic of a biofilm, wherein the biofilm detection unit includes an inner lumen electrode and an outer surface electrode for measuring impedance; and
electric circuitry configured to provide an output signal indicative of a result of the detection.

* * * * *